(12) United States Patent
Gerlach et al.

(10) Patent No.: US 7,205,299 B2
(45) Date of Patent: *Apr. 17, 2007

(54) INDOLE DERIVATIVES HAVING AN APOPTOSIS-INDUCING EFFECT

(75) Inventors: Matthias Gerlach, Brachttal (DE); Tilmann Schuster, Frankfurt (DE); Peter Ernig, Bruchköbel (DE); Peter Schmidt, Schöneck (DE); Silke Baasner, Schöneck (DE); Eckhard Günther, Maintal (DE)

(73) Assignee: Zentaris GmbH, Frankfurt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/858,751

(22) Filed: Jun. 2, 2004

(65) Prior Publication Data

US 2004/0266762 A1  Dec. 30, 2004

Related U.S. Application Data

(60) Provisional application No. 60/476,277, filed on Jun. 5, 2003, provisional application No. 60/476,794, filed on Jun. 6, 2003, provisional application No. 60/572,025, filed on May 17, 2004.

(30) Foreign Application Priority Data

Jun. 6, 2003 (EP) .................. 03012868
May 15, 2004 (EP) .................. 04011598

(51) Int. Cl.
*A61K 31/5025* (2006.01)
*A61K 31/4709* (2006.01)
*A61K 31/4427* (2006.01)
*C07D 487/02* (2006.01)
*C07D 215/38* (2006.01)

(52) U.S. Cl. ............... 514/248; 514/314; 514/339; 514/406; 544/236; 546/171; 546/278.1; 548/362.5

(58) Field of Classification Search ........... 546/171, 546/278.1; 548/362.5; 514/248, 314, 339, 514/406

See application file for complete search history.

(56) References Cited

U.S. PATENT DOCUMENTS

| | | |
|---|---|---|
| 6,232,327 B1 | 5/2001 | Nickel et al. |
| 6,251,923 B1 | 6/2001 | Hofgen et al. |
| 6,693,119 B2 | 2/2004 | Nickel et al. |
| 2003/0092751 A1 | 5/2003 | Koya et al. |
| 2003/0100597 A1 | 5/2003 | Ernig et al. |
| 2003/0114511 A1 | 6/2003 | Nickel et al. |
| 2003/0181482 A1 | 9/2003 | Chen et al. |
| 2004/0029858 A1 | 2/2004 | Menta et al. |

FOREIGN PATENT DOCUMENTS

| | | |
|---|---|---|
| WO | WO 00/67802 | 11/2000 |
| WO | WO03/022280 | 3/2003 |

OTHER PUBLICATIONS

Wen-Tai Li, et al., Synthesis and Biological Evaluation of N-Heterocyclic Indolyl Glyoxylamides as Orally Active Anticancer Agents, J. Med. Chem. 2003, 46, 1706-1715.

*Primary Examiner*—Kamal A. Saeed
*Assistant Examiner*—Jason M. Nolan
(74) *Attorney, Agent, or Firm*—Goodwin Procter LLP

(57) ABSTRACT

The invention relates to indole derivatives which are used as drugs for treating tumor diseases, in particular when there is drug resistance against other active compounds and where there is a metastasizing carcinoma.

21 Claims, 3 Drawing Sheets

INDOLE DERIVATIVES HAVING AN APOPTOSIS-INDUCING EFFECT

CROSS-REFERENCE TO RELATED APPLICATIONS

This application claims the benefit of priority to U.S. Provisional Application Nos. 60/476,277 filed on Jun. 5, 2003, 60/476,794 filed on Jun. 6, 2003 and 60/572,025 filed on May 17, 2004 and European Patent Application Nos. 03012868.0 filed on Jun. 6, 2003 and 04011598.2 filed on May 15, 2004, all of which are incorporated herein by reference in their entirety.

FIELD OF THE INVENTION

The present invention relates to novel indole derivatives which have a better biological effect, which are better tolerated, which exhibit better oral bioavailability and which are employed as drugs for treating tumor diseases, in particular when drug resistance exists against other active compounds and when a carcinoma is metastasizing.

BACKGROUND OF THE INVENTION

The treatment of cancer diseases is of great importance in medicine. There is a worldwide need for effective cancer therapies in order to achieve a treatment which is appropriate to a patient and is target-orientated. This can be seen in the large number of scientific studies which have recently appeared in the fields of applied oncology and fundamental research relating to cancer therapy.

The effects of tumor inhibitors are due to a very wide variety of mechanisms, only some of which are known. It is not unusual for known tumor drugs to be found to have new mechanisms of action. This is also to be expected in the case of the compounds according to the invention. Many tumor drugs act by way of mechanisms such as blockading the mechanism of cell division in the cell, preventing the tumor from being supplied with nutrients and oxygen (antiangiogenesis), preventing metastasis, preventing the reception and the onward transmission of growth signals to the tumor cell or forcing the tumor cell into programed cell death (apoptosis).

Because they have different mechanisms of action, including interacting with different intracellular targets, the clinically relevant cytostatic agents are frequently administered in combination in order to achieve a synergistic therapeutic effect.

Indole derivatives are used in a great variety of ways as pharmacodynamically active compounds and as building blocks for synthesis in pharmaceutical chemistry. Documents WO 99/51224 A1 and WO 01/22954 A1 describe indol-3-yl derivatives which have an antineoplastic effect and which can be substituted by a large number of groups, including by 2-, 3-, 4- and 8-quinoline radicals or 2-, 3-, 4-, 5- and 6-pyridine radicals. A 2-methyl-8-quinolinyl group is mentioned in Example 60 as being a substituent on the amide group. However, no biological properties are mentioned. WO 99/55696 A1 describes substituted hydroxyindoles as being inhibitors of phosphodiesterase 4. However, the compounds according to the invention are not reported to have any antineoplastic activity, nor is it suggested that they might have this activity.

WO 02/08225 A1 describes 2-(1H-indol-3-yl)-2-oxoacetamide derivatives which have an antineoplastic effect in relation to solid tumors. However, there is no mention of specific implementation examples containing quinoline, pyridopyrazine or indazolyl radicals.

Patent specification WO 00/67802 describes indole-3-glyoxylamides which are substituted by relatively long-chain fatty acids as being potential antineoplastic agents. However, there is no mention of specific implementation examples containing quinoline, pyridopyrazine or indazolyl radicals. Nor are any biological data given with regard to such implementation examples.

The publication by W.-T. Li et al. (J. Med. Chem. 2003, 46, 1706 ff.) describes N-heterocyclic indolylglyoxylamides as being orally active compounds which possess antineoplastic activity. However, no information is provided as regards their mechanism of action.

Patent application WO 03/022280 A2 describes 3-glyoxylamideindoles and their use as drugs for antineoplastic treatment. Their general formula also includes 6-quinoline derivatives. In addition, two examples containing a 6-quinoline radical are mentioned as implementation examples and verified by means of biological results. However, there is no mention of specific implementation examples containing pyridopyrazine or indazolyl radicals.

U.S. application Ser. No. 03/0181482 A1 describes novel indolylglyoxylamides. In this case, the compounds according to the invention are described as being antineoplastic agents possessing cytotoxic activity and as being angiogenesis inhibitors. In addition to this, a 6-quinoline derivative is shown as an implementation example (compound 3; p. 10) and verified by means of antiproliferative data (see p. 19; Tables 1a and 1b) and antiangiogenic properties (see p. 20). However, there is no mention of specific implementation examples containing pyridopyrazine or indazolyl radicals.

The Applicant's WO 02/10152 A2 already describes a second class of indole derivatives for treating tumors. In this document, the active compound N-(2-methyl-6-quinolyl)-[1-(4-chlorobenzyl)indol-3-yl]glyoxylamide, inter alia, was tested for its antiproliferative effect on a variety of tumor cell lines.

Clinically tested compounds which either bind to the microtubules (paclitaxel and vincristine) or inhibit topoisomerase II (doxorubicin, etoposide and mitoxantrone) are at present being successfully employed in cancer therapy against, inter alia, breast cancer, ovarian cancer, stomach cancer and lung cancer, and in Kaposi's sarcoma and in leukemias. However, their use is limited by the appearance of drug resistances and also by serious neurological, gastrointestinal, cardiovascular and hepatic side effects.

SUMMARY OF THE INVENTION

An object underlying the invention is now to make available cytotoxic substances which possess combined mechanisms of action and which are suitable for treating a large number of tumors, in particular when active compound resistances exist against other drugs and when carcinomas are metastasizing.

DETAILED DESCRIPTION OF THE INVENTION

Figure 1:
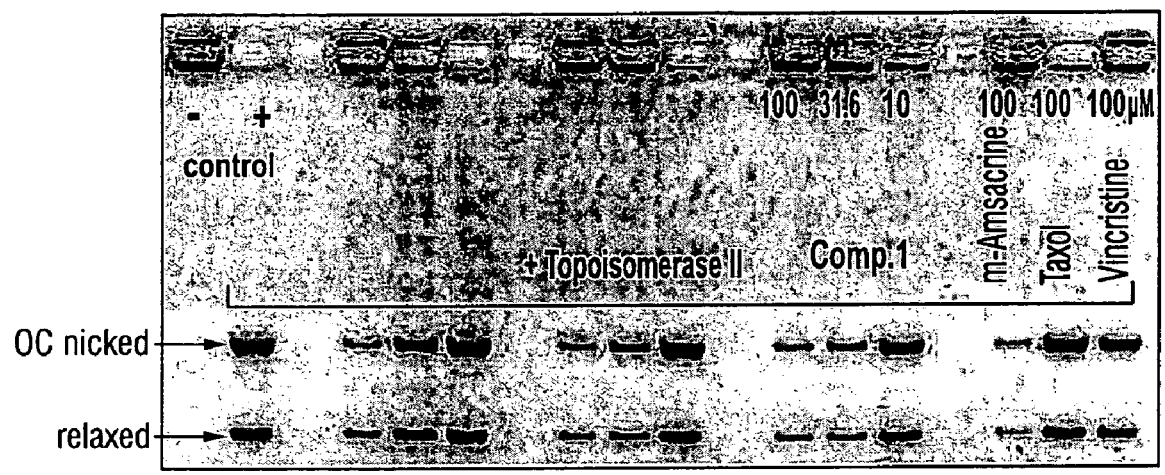
FIG. 1 is a photograph of kDNA assay.

This object is achieved by indole derivatives of the general formula I

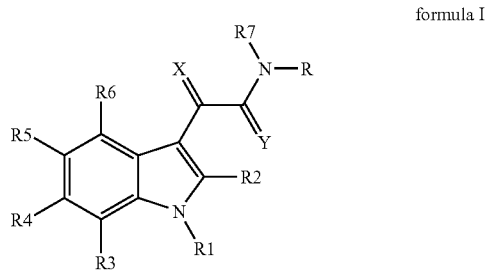

formula I in which
R: is a saturated, unsaturated or aromatic, substituted or unsubstituted ($C_2$–$C_{14}$)-heterocycle which contains one or more heteroatoms selected from the group N, O and S and which is directly linked to the amide nitrogen, with the heterocycle preferably being
  (i) unsubstituted or substituted 5-, 6-, 7-quinolyl,
  (ii) unsubstituted or substituted 2-, 3-, 6-, 7- and 8-pyridopyrazinyl,
  (iii) unsubstituted or substituted 3-, 4-, 5-, 6- and 7-indazolyl,
  (iv) unsubstituted or substituted 2-, 3-, 4-, 5- and 6-pyridyl,
  (v) unsubstituted or substituted 3-, 4- and 5-isoxazolyl,
  (vi) unsubstituted or substituted 3-, 4- and 5-isothiazolyl,
R1: is unsubstituted or substituted alkyl-aryl,
R2: is
  (i) hydrogen,
  (ii) unsubstituted or substituted ($C_1$–$C_6$)-alkyl,
R3–R6: are
  (i) hydrogen
  (ii) unsubstituted or substituted ($C_1$–$C_6$)-alkyl,
  (iii) unsubstituted or substituted ($C_3$–$C_7$)-cycloalkyl,
  (iv) amino, mono- ($C_1$–$C_4$)-alkylamino, di-($C_1$–$C_4$)-alkylamino,
  (v) halogen,
  (vi) ($C_1$–$C_4$)-alkyl which is substituted by one or more fluorine atoms, preferably trifluoromethyl group,
  (vii) cyano, straight-chain or branched cyano-($C_1$–$C_6$)-alkyl,
  (viii) ($C_1$–$C_6$)-alkylcarbonyl,
  (ix) carboxyl, ($C_1$–$C_4$)-alkoxycarbonyl, carboxy-($C_1$–$C_6$)-alkyl or ($C_1$–$C_6$)-alkoxycarbonyl-($C_1$–$C_6$)-alkyl,
  (x) hydroxyl,
  (xi) —($C_1$–$C_6$)-alkoxy,
  (xii) aryl-($C_1$–$C_4$)-alkoxy, preferably benzyloxy,
  (xiii) ($C_1$–$C_6$)-alkoxycarbonylamino, ($C_1$–$C_6$)-alkoxycarbonylamino-($C_1$–$C_6$)-alkyl,
R7: is
  ($C_1$–$C_6$)-alkylcarbonyl, preferably acetyl or propionyl,
  ($C_1$–$C_6$)-alkoxycarbonyl, preferably methoxy-carbonyl, ethoxycarbonyl or propoxycarbonyl, and
X, Y: are oxygen or sulfur, the tautomers and stereoisomers, including the diastereomers and enantiomers, thereof, and also the physiologically tolerated salts thereof.

When R is an unsubstituted or substituted 2-, 3-, 4-, 5- or 6-pyridyl group and R1–R6 have the abovementioned meaning, R7 must not, in this case, be an acetyl radical or a tert-butyloxycarbonyl group.

The invention furthermore relates to indole derivatives of the formula I in which

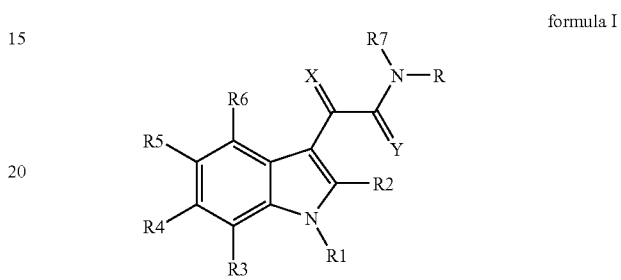

formula I

R: is, directly linked to the amide nitrogen,
  (i) substituted 6-quinolyl, unsubstituted or substituted 7-quinolyl, where 2-methyl-6-quinolyl is excluded and where, when X is a sulfur atom, R can also be unsubstituted 6-quinolyl.
  (ii) unsubstituted or substituted 2-, 3-, 6-, 7- and 8-pyridopyrazinyl,
  (iii) unsubstituted or substituted 3-, 4-, 5-, 6- and 7-indazolyl,
R1: is unsubstituted or substituted alkyl-aryl,
R2: is hydrogen
R3–R6: are
  (xiv) hydrogen
  (xv) unsubstituted or substituted ($C_1$–$C_6$)-alkyl,
  (xvi) unsubstituted or substituted ($C_3$–$C_7$)-cycloalkyl,
  (xvii) amino, mono-($C_1$–$C_4$)-alkylamino, di-($C_1$–$C_4$)-alkylamino,
  (xviii) halogen,
  (xix) ($C_1$–$C_4$)-alkyl which is substituted by one or more fluorine atoms, preferably trifluoromethyl group,
  (xx) cyano, straight-chain or branched cyano-($C_1$–$C_6$)-alkyl,
  (xxi) ($C_1$–$C_6$)-alkylcarbonyl,
  (xxii) carboxyl, ($C_1$–$C_4$)-alkoxycarbonyl, carboxy-($C_1$–$C_6$)-alkyl or ($C_1$–$C_6$)-alkoxy-carbonyl-($C_1$–$C_6$)-alkyl,
  (xxiii) —($C_1$–$C_6$)-alkoxy,
  (xxiv) aryl-($C_1$–$C_4$)-alkoxy, preferably benzyloxy,
  (xxv) ($C_1$–$C_6$)-alkoxycarbonylamino, ($C_1$–$C_6$)-alkoxycarbonylamino-($C_1$–$C_6$)-alkyl,
and
R7: hydrogen
X, Y: are oxygen or sulfur, the tautomers and stereoisomers, including the diastereomers and enantiomers, thereof, and also the physiologically tolerated salts thereof.

The present invention is a further development of the invention which is described in WO 02/10152. It was observed that the indole derivatives which were obtained by replacing the 2-methyl-6-quinolyl group with unsubstituted or substituted 2-, 3-, 6-, 7- and 8-pyridopyrazinyl or unsubstituted or substituted 3-, 4-, 5-, 6- and 7-indazolyl exhibit a superior antiproliferative effect on a variety of tumor cell lines.

If was furthermore observed that the compounds according to the invention exert a powerful cytotoxic effect which can be due to a very wide variety of different mechanisms. One mechanism of the compounds according to the invention, which is demonstrated in the invention, is based on inhibiting tubulin polymerization and on inhibiting topoisomerase II. This leads to the arrest of tumorigenic cells in the G2M phase. In addition to this, the compounds according to the invention induce apoptosis.

It was furthermore observed that the compounds according to the invention have a superior solubility in water and consequently also a superior oral bioavailability.

In addition, it was demonstrated that introducing an acetyl radical as the R7 radical resulted in the compounds according to the invention having superior in-vivo activity while at the same time being better tolerated.

The substance class which is described in the invention should open up the possibility of obtaining antineoplastic medication which is lower, longer lasting and better tolerated than can be achieved using the conventional cytostatic agents. In particular, it should be possible to circumvent the disadvantageous development of resistance, as is known to occur in the case of many antineoplastic agents. The effect augmentation which is achieved using the indole derivatives according to the invention should make drug usage more efficient. In addition to this, it ought to be possible to extend the treatment to cases which are resistant to therapy.

In a preferred embodiment, R1 is 4-chlorobenzyl, R2–R6 are hydrogen, R is heterocycle and R7 is alkylcarbonyl or alkoxycarbonyl in the indole derivative of the formula I.

In another preferred embodiment, R is unsubstituted 5-quinolyl, unsubstituted 6-quinolyl or unsubstituted 7-quinolyl and R7 is acetyl or propionyl in the indole derivative of the formula I.

In another preferred embodiment, R is unsubstituted 5-quinolyl, unsubstituted 6-quinolyl or unsubstituted 7-quinolyl and R7 is methoxycarbonyl, ethoxycarbonyl or propionoxycarbonyl in the indole derivative of the formula I.

Some terms which are used in the description and the patent claims are defined below.

In connection with "heterocycle", the term is understood as meaning, insofar as not explicitly mentioned above, pyrrole, furan, thiophene, pyrazole, thiazole, indole, oxazole, imidazole, isothiazole, isoxazole, 1,2,3-triazole, 1,2,4-triazole, 1,2,4-oxadiazole, 1,3,4-oxadiazole, 1,2,5-thiadiazole, 1,3,4-thiadiazole, tetrazole, pyridine, pyrimidine, pyridazine, pyrazine, benzofuran, indazole, carbazole, benzoxazole, benzimidazole, benzothiazole, benzotriazole, quinoline, cinnoline, quinoxaline, quinazoline, phthalazine, pyridopyrazine, 1,2,3-triazine, 1,2,4-triazine, 1,3,5-triazine, purine, pteridine, acridine and phenanthridine.

Within the meaning of this invention, the expression "alkyl" encompasses acyclic saturated or unsaturated hydrocarbons which may be straight-chain or branched. In connection with "alkyl", the term "substituted" is understood as being, within the meaning of this invention and insofar as not explicitly defined above, the replacement of a hydrogen radical with F, Cl, Br, I, CN, $NH_2$, NH-alkyl, NH-cycloalkyl, OH or O-alkyl, where polysubstituted radicals are to be understood as meaning those which are substituted more than once, e.g. twice or three times, either at different atoms or at identical atoms, for example three times at the same C atom, as in the case of —$CF_3$ and —$CH_2CF_3$, or at different sites, as in the case of —CH(OH)—$CH_2$—$CH_2$—$CHCl_2$. The polysubstitution can be effected using the same substituents or different substituents.

The expression "alkyl-aryl" means ($C_1$–$C_6$)-alkyl-($C_1$–$C_{14}$)-aryl and preferably ($C_1$–$C_6$)-alkyl-$C_6$-aryl.

In regard to "alkyl-aryl" and to "cycloalkyl", "substituted once or more than once" is understood, within the meaning of this invention and insofar as not explicitly mentioned above, as meaning the single or multiple, for example twofold, threefold or fourfold replacement of one or more hydrogen atoms in the ring system with F, Cl, Br, I, CN, $NH_2$, NH-alkyl, OH, O-alkyl, $CF_3$, alkyl, ($C_6$–$C_{10}$)-aryl, ($C_6$–$C_{10}$)-aryl-($C_1$–$C_6$)-alkyl and/or heterocyclyl at one or, where appropriate, different atoms (with it being possible for a substituent, for its part, to be substituted, where appropriate). In this connection, the multiple replacement is effected using the same substituent or using different substituents.

With regard to "heterocycle", "substituted once or more than once" is understood, within the meaning of this invention and insofar as not explicitly mentioned above, as being the single or multiple, e.g. twofold, threefold or fourfold, replacement of one or more hydrogen atoms in the ring system with F, Cl, Br, I, nitro, amino, $C_1$–$C_6$-alkyl, preferably methyl, mono-($C_1$–$C_6$)-alkylamino, di-($C_1$–$C_6$)-alkylamino, hydroxyl, $C_1$–$C_6$-alkoxy, benzyloxy, carboxyl, ($C_1$–$C_6$)-alkoxycarbonyl, ($C_1$–$C_6$)-alkoxycarbonylamino or ($C_1$–$C_6$)-alkyl which is substituted, once or more than once, by fluorine, preferably trifluoromethyl, ($C_6$–$C_{10}$)-aryl and/or ($C_6$–$C_{10}$)-aryl-($C_1$–$C_6$)-alkyl at one or, where appropriate, different atoms (with it being possible for a substituent for its parts to be substituted, where appropriate). In this connection, the multiple replacement is effected using the same substituents or using different substituents.

Provided the compounds according to the invention of the general formula I possess at least one center of asymmetry, they can be present in the form of their racemates, in the form of the pure enantiomers and/or diastereomers or in the form of mixtures of these enantiomers and/or diastereomers. The stereoisomers can be present in the mixtures in any arbitrary proportions. Provided this is possible, the compounds according to the invention can be present in the form of the tautomers.

Thus, methods which are known per se can be used, for example, to separate the compounds according to the invention of the general formula I which possess one or more chiral centers and occur as racemates into their optical isomers, that is enantiomers or diastereomers. The separation can be effected by means of column separation on chiral phases or by means of recrystallization from an optically active solvent or using an optically active acid or base or by means of derivatizing with an optically active reagent, such as an optically active alcohol, and subsequently cleaving off the residue.

If they contain a sufficiently acidic group, such as the carboxyl group, the compounds according to the invention of the general formula I can be converted into their physiologically tolerated salts using inorganic and/or organic bases. Examples of suitable inorganic bases are sodium hydroxide, potassium hydroxide and calcium hydroxide while examples of suitable organic bases are ethanolamine, diethanolamine, triethanolamine, cyclohexylamine, dibenzylethylenediamine and lysine. In this connection, the stoichiometry of the salts of the compounds according to the invention which are formed can be either an integral or a nonintegral multiple of one.

If they possess a sufficiently basic group, such as a secondary or tertiary amine, the compounds according to the invention of the general formula I can be converted into salts using inorganic and organic acids. The pharmaceutically acceptable salts of the compounds according to the invention in accordance with the general structure I are preferably formed with hydrochloric acid, hydrobromic acid, sulfuric acid, phosphoric acid, methanesulfonic acid, p-toluenesulfonic acid, carbonic acid, formic acid, acetic acid, trifluoroacetic acid, oxalic acid, malonic acid, maleic acid, succinic acid, tartaric acid, pyruvic acid, malic acid, embonic acid, mandelic acid, fumaric acid, lactic acid, citric acid, glutamic acid or aspartic acid. The salts which are formed are, inter alia, hydrochlorides, hydrobromides, sulfates, phosphates, methanesulfonates, sulfoacetic acid, tosylates, carbonates, hydrogen carbonates, formates, acetates, triflates, oxalates, malonates, maleates, succinates, tartrates, malates, embonates, mandelates, fumarates, lactates, citrates and glutaminates. In this connection, the stoichiometry of the salts of the compounds according to the invention which are formed can be an integral or nonintegral multiple of one.

Preference is likewise given to solvates and, in particular, hydrates of the compounds I according to the invention which can be obtained, for example, by crystallization from a solvent or from aqueous solution. In this connection, one, two, three or any arbitrary number of solvate or water molecules can combine with the compounds according to the invention to form solvates and hydrates.

It is known that chemical substances form solids which are present in different states of order which are termed polymorphic forms or modifications. The different modifications of a polymorphic substance can differ greatly in their physical properties. The compounds according to the invention of the general formula I can be present in different polymorphic forms, with it being possible for particular modifications to be metastable.

Both the compounds of the formula I and their salts are biologically active. The compounds of the formula I can be administered in free form or as salts with physiologically tolerated acids or bases.

The compounds of the general formula can be administered orally, rectally, via the buccal route (e.g. sublingually), parenterally (e.g. subcutaneously, intramuscularly, intradermally or intravenously), topically or transdermally.

The invention furthermore relates to drugs having a content of at least one of the compounds of the formula I, or their salts with physiologically tolerated inorganic or organic acids, and, where appropriate, pharmaceutically utilizable carrier substances and/or diluents or auxiliary substances.

These drugs are used for treating tumor diseases, in particular for treatment in connection with tumor diseases involving drug resistance against other active compounds and/or in connection with tumor diseases involving a metastasizing carcinoma.

Examples of suitable administration forms are tablets, sugar-coated tablets, capsules, solutions for infusion or ampoules, suppositories, plasters, powder preparations which can be used for inhalation, suspensions, creams and ointments.

The compounds according to the invention can also be dispersed in a microparticulate, e.g. nanoparticulate, composition.

In detail, the therapeutically valuable properties which have been found relate to the following advantages:
the compounds according to the invention are characterized by powerful antiproliferative properties;
the compounds according to the invention inhibit tubulin polymerization;
the compounds according to the invention inhibit topoisomerase II;
the compounds according to the invention arrest dividing cells in the G2/M phase;
the compounds according to the invention induce apoptosis;
the compounds according to the invention are characterized by powerful antineoplastic activities in vivo while also being better tolerated;
the compounds according to the invention of the formula I are active in vitro on mdr-resistant cell lines, in contrast to paclitaxel, vincristine, doxorubicin or etoposide.

Greatest preference is given to compounds according to the general formula I which are included in the following selection:
2-[1-(4-chlorobenzyl)-1H-indol-3-yl]-2-oxo-N-pyrido[2,3-b]pyrazin-7-ylacetamide (1)
2-[1-(4-chlorobenzyl)-1H-indol-3-yl]-N-(1H-indazol-5-yl)-2-oxoacetamide (4)
N-{2-[1-(4-chlorobenzyl)-1H-indol-3-yl]-2-oxoacetyl}-N-quinolin-6-ylacetamide (2)
methyl {2-[1-(4-chlorobenzyl)-1H-indol-3-yl]-2-oxoacetyl}quinolin-6-ylcarbamate (3)
ethyl {2-[1-(4-chlorobenzyl)-1H-indol-3-yl]-2-oxoacetyl}quinolin-6-ylcarbamate (5)
propyl {2-[1-(4-chlorobenzyl)-1H-indol-3-yl]-2-oxoacetyl}quinolin-6-ylcarbamate (6)
N-{2-[1-(4-chlorobenzyl)-1H-indol-3-yl]-2-oxoacetyl}-N-quinolin-6-ylpropionamide (7)
ethyl {2-[1-(4-chlorobenzyl)-1H-indol-3-yl]-2-oxoacetyl}pyridin-4-ylcarbamate (8)
2-[1-(4-chlorobenzyl)-1H-indol-3-yl]-N-quinolin-6-yl-2-thioxoacetamide (11)

Compounds (1), (4) and (11) are compounds in which the radical R7 is hydrogen. Compounds (2), (3), (5) and (6) to (8) contain an alkylcarbonyl group of an alkoxycarbonyl group as the group R7.

The following compounds (9), (10), (12), (13), (14) and (15) are compounds which were also investigated for the purposes of comparison. Compounds (9), (10), (14) and (15) are known from the prior art. Compound (9) is described in the Applicant's WO 02/10152, compound (10) is described in WO 03/022280, compound (13) is covered by the claims in WO 02/08225 A1, and compounds (12), (14) and (15) are covered by the claims in WO 99/51224 A1 and WO 01/22954.
2-[1-(4-chlorobenzyl)-1H-indol-3-yl]-N-(2-methylquinolin-6-yl)-2-oxoacetamide (9)
2-[1-(4-chlorobenzyl)-1H-indol-3-yl]-2-oxo-N-quinolin-6-ylacetamide (10)
2-[1-(4-chlorobenzyl)-1H-indol-3-yl]-2-oxo-N-quinolin-8-ylacetamide (12)
2-[1-(4-chlorobenzyl)-1H-indol-3-yl]-N-isoquinolin-5-yl-2-oxoacetamide (13)
2-[1-(4-chlorobenzyl)-1H-indol-3-yl]-2-oxo-N-pyridin-4-ylacetamide (14)
2-[1-(4-fluorobenzyl)-1H-indol-3-yl]-N-(2-methylquinolin-8-yl)-2-oxoacetamide (15)

Compounds of the general formulae Ia and Ib of the scheme can be obtained in accordance with the following Scheme 1:

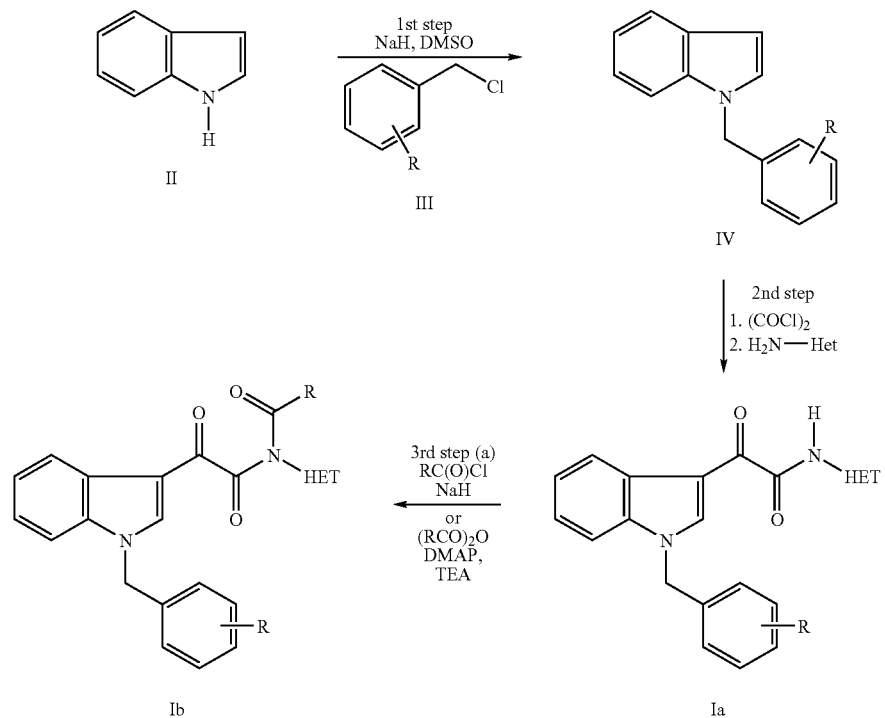
The compounds of the general formula Ic, in which X=S, can be prepared in accordance with Scheme 2:
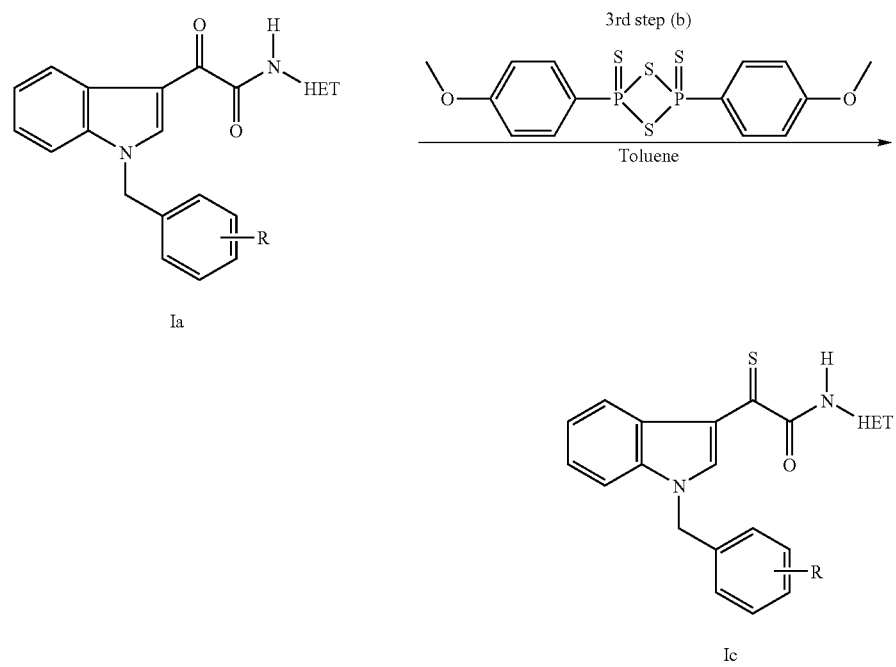

Compounds of the general formula Ic, in which Y=S, can be obtained using methods known from the literature (W.-D. Malmberg et al. Liebigs Ann. Chem. 10, 1983; 1649–1711).

The starting compounds II, III and IV can either be obtained commercially or prepared using procedures which are known per se. The starting compounds II, III and IV are valuable intermediates for preparing the indole derivatives according to the invention of the formula I.

For the preparation of the starting compounds and target compounds, reference may be made, for example, to the following standard works of organic synthesis, the content of which is hereby intended to be incorporated into the disclosure of the present application:

Houben-Weyl, Volume E 7a (Part 1) pp. 290–492, pp. 571–740

Houben-Weyl, Volume E 7a (Part 2) pp. 119–156, pp. 205–686, pp. 157–204

The monograph "Heterocyclic Compounds" (Elderfield),
Volume 1, pp. 119–207, pp. 397–616
Volume 3, pp. 1–274
Volume 6, pp. 101–135, pp. 234–323

The monograph "Comprehensive Organic Chemistry" (S. D. Barton, W. D. Ollis)
Volume 4, pp. 155–204, pp. 205–232, pp. 493-564

The skilled person is familiar, on account of his specialist knowledge, with the solvents and auxiliary agents, and reaction parameters, such as reaction temperature and reaction duration, which are to be used, where appropriate.

The following compounds, whose inclusion in the survey below is evident from their respective chemical designations, were synthesized in accordance with these general directions for steps 1, 2 and 3, as based on synthesis Schemes 1 and 2. The compounds according to the invention were characterized analytically by means of their melting points and/or by means of 1H NMR spectroscopy and/or mass spectroscopy.

The chemicals and solvents employed were either obtained commercially from the customary suppliers (Acros, Avocado, Aldrich, Fluka, Lancaster, Maybridge, Merck, Sigma, TCI, etc.) or synthesized.

The invention will be explained in more detail with the aid of the following examples without being restricted to them.

EXAMPLES

Example 1

Reaction in Accordance with Scheme 1, 1st Step

Preparation of 1-(4-chlorobenzyl)indole

A solution of 5.86 g (0.05 mol) of indole in 25 ml of DMSO is added to a mixture of 1.32 g of sodium hydride (0.055 mol, mineral oil suspension) in 50 ml of dimethyl sulfoxide. The resultant mixture is heated at 60° C. for 1.3 hours; after that, it is allowed to cool down and 17.7 g (0.11 mol) of 4-chlorobenzyl chloride are added dropwise. The solution is heated to 60° C. and allowed to stand overnight; it is then poured into 200 ml of water while stirring. This mixture is extracted several times with a total of 75 ml of $CH_2Cl_2$, after which the organic phase is dried with anhydrous sodium sulfate and filtered and the filtrate is evaporated in vacuo.

Yield: 11.5 g (95% of theory)

Example 2

Reaction in Accordance with the 2nd Step of Scheme 1

2-[1-(4-Chlorobenzyl)-1H-indol-3-yl]-2-oxo-N-pyrido-[2,3,b]pyrazin-7-ylacetamide (1)

A solution of 10.2 g (10.7 mMol) of 1-(4-chlorobenzyl)-indole in 200 ml of ether is added dropwise, at 0° C. and under nitrogen, to a solution of 1.12 ml of oxalyl chloride in 50 ml of ether. The mixture is heated to reflux for 2 hrs. and the solvent is subsequently evaporated off. 30 ml of DMF are then added to the residue, after which 1.93 g (13.9 mMol) of potassium carbonate are added and the suspension is cooled down to 0° C.; a solution of 1.57 g (10.7 mMol) of amino component in 10 ml of DMF is then added dropwise. The reaction mixture is left to stir overnight at room temperature. It is finally stirred into ice water and the resulting precipitate is filtered off with suction. The crude product which is obtained is chromatographed on 100 g of silica gel using n-heptane/ethyl acetate=4:1.

Yield: 3.23 g (68.0%).

m.p.: 250° C.

1H-NMR (DMSO-D6) δ=11.56 (s, 1H), 9.53 (d, 1H), 9.12 (s, 1H), 9.09 (d, 1H), 9.04 (s, 1H), 8.32 (d, 1H), 7.6 (d, 1H), 7.40 (d, 2H), 7.35 (m, 3H), 7.32 (m, 2H), 5.64 (s, 2H) ppm.

Example 3

Reaction in Accordance with the 3rd Step (a) of Scheme 1

N-{2-[1-(4-Chlorobenzyl)-1H-indol-3-yl]-2-oxoacetyl}-N-quinolin-6-ylacetamide (2)

0.833 g (6.82 mMol) of DMAP, 1.38 g (13.6 mMol) of triethylamine and 13.9 g (136 mMol) of acetic anhydride are added, under nitrogen, to a stirred solution of 6.0 g (13.6 mMol) of 2-[1-(4-chlorobenzyl)-1H-indol-3-yl]-2-oxo-N-quinolin-6-ylacetamide in 60 ml of DMF. The reaction mixture is stirred at room temperature for 10 minutes and, after that, poured into 200 ml of ethyl acetate. After 300 ml of water have been added, the mixture is shaken in a separating funnel after which the two phase separate. Precipitation begins after 20 minutes. The pale yellow crystals are filtered off and dried in vacuo at 60° C.

Yield: 4.04 g (61.5%)

m.p.: 122.9° C.

$^1$H-NMR (600 MHz, DMSO-D6) δ=9.02 (d, 1H), 8.54 (s, 1H), 8.44 (d, 1H), 8.21 (d, 1H), 8.17 (d, 1H), 8.10 (m, 1H), 7.88 (m, 1H), 7.65 (m, 1H), 7.58 (m, 1H), 7.44 (d, 2H), 7.33 (d, 2H), 7.28 (m, 2H), 5.60 (s, 2H), 2.15 (s, 3H).

MS(ESI) m/z 482.1 (MH$^+$), (theor. 481.94)

Example 4

Reaction in Accordance with the 3rd Step (a) of Scheme 1

Methyl {2-[1-(4-chlorobenzyl)-1H-indol-3-yl]-2-oxoacetyl}quinolin-6-ylcarbamate (3)

930.2 mg (27.3 mMol) of NaH (as a 60% strength dispersion in mineral oil) are added, under nitrogen, to a cooled, stirred solution of 10.0 g (22.7 mMol) of 2-[1-(4-chlorobenzyl)-1H-indol-3-yl]-2-oxo-N-quinolin-6-ylacetamide in 500 ml of dry THF. The solution is stirred at 0° C.

until a yellow precipitate separates out and, after that, stirred for a further 15 minutes. After that, 2.58 g (27.3 mMol) of methyl chloroformate are added dropwise at a temperature below +5° C. The reaction is monitored by thin layer chromatography (eluent: n-heptane/ethyl acetate 1/1 RF=0.11). The reaction mixture is poured into water and the resulting mixture is extracted with ethyl acetate; the organic phase is washed with a saturated solution of sodium chloride and dried over anhydrous MgSO4. Evaporating off the solvent yields a crude product, which is purified by column chromatography (n-heptane/acetone 2/1) in order to give 3. Thin layer chromatography shows that 3 still contains slight impurities, which can be removed by stirring the crude 3 with acetone for 1 h. Filtration yields 3 as pale yellow crystals.

Yield: 3.0 g (25.6%)

m.p.: 178.5° C.

$^1$H-NMR (600 MHz, DMSO-D6) δ=9.02 (d, 1H), 8.58 (s, 1H), 8.47 (d, 1H), 8.17 (m, 3H), 7.84 (m, 1H), 7.63 (m, 2H), 7.44 (d, 2H), 7.34 (m, 4H), 5.60 (s, 2H), 3.65 (s, 3H).

MS(ESI) m/z 498.2 (MH$^+$), (theor. 497.94)

Example 5

Reaction in Accordance with the 3rd Step (b) of Scheme 2

Preparing 2-[1-(4-chlorobenzyl)-1H-indol-3-yl]-N-quinolin-6-yl-2-thioxoacetamide (11)

3.68 g (9.1 mMol) of 2,4-bis(4-methoxyphenyl)-1,3-dithia-2,4-diphosphetane-2,4-disulfide are added, under nitrogen, to a suspension of 4.00 g (9.1 mMol) of 2-[1-(4-chlorobenzyl)-1H-indol-3-yl]-2-oxo-N-quinolin-6-ylacetamide in 200 ml of toluene, after which the mixture is heated at 75° C. for 3 h. The residue which has formed is filtered off in the hot from the reaction solution and subsequently washed with 100 ml of methylene chloride. The filtrate is concentrated in vacuo and the residue is chromatographed on flash silica gel (eluent: methylene chloride/methanol 99:1). The product fractions are filtered on flash silica gel (eluent: n-heptane/ethyl acetate 1:1) after the solvent has been removed once more.

Yield: 0.46 g (11% of theory)

ESI-MS: m/e 456.1 (MH$^+$), (theor. 455.97)

1H-NMR (DMSO-D6) δ=10.89 (s, 1H), 8.8 (s, 1H), 8.75 (s, 1H), 8.55 (s, 1H), 8.12 (d, 1H), 8.35 (d, 1H), 8.0 (d, 1H), 7.93 (d, 1H), 7.63 (d, 1H), 7.50 (m, 1H), 7.4 (m, 3H), 7.3 (m, 3H), 5.6 (s, 2H) ppm.

The following compounds of the formula I were simplified in analogy with the synthesis route in Scheme 1 and in accordance with Examples 2 and 3.

Example 6

2-[1-(4-Chlorobenzyl)-1H-indol-3-yl]-N-(1H-indazol-5-yl)-2-oxoacetamide (4)

m.p.: 203° C.

H-NMR (DMSO-D$_6$) δ=13.02 (s, 1H), 10.7 (s, 1H), 9.04 (s, 1H), 8.48 (s, 1H), 8.42 (d, 1H), 8.06 (s, 1H), 7.73 (d, 1H), 7.6 (d, 1H), 7.55 (d, 1H), 7.40 (d, 2H), 7.28-7.35 (m, 4H), 5.63 (s, 2H) ppm Example 7

Ethyl {2-[1-(4-chlorobenzyl)-1H-indol-3-yl]-2-oxoacetyl}quinolin-6-ylcarbamate (5)

m.p.: 199° C.

$^1$H NMR (600 MHz, DMSO-D6) δ=9.02 (m, 1H), 8.60 (s, 1H), 8.48 (d, 1H), 8.15 (m, 3H), 7.83 (m, 1H), 7.63 (m, sH), 7.43 (d, 2H), 7.32 (m, 4H), 5.60 (s, 2H), 4.15 (q, 2H), 0.95 (t, 3H).

MS (ESI) m/z 514.2, 512.1 (MH$^+$), (theor. 511.97)

Example 8

Propyl {2-[1-(4-chlorobenzyl)-1H-indol-3-yl]-2-oxoacetyl}quinolin-6-ylcarbamate (6)

m.p.: 164° C.

$^1$H-NMR (600 MHz, DMSO-D6) δ=9.02 (m, 1H), 8.60 (s, 1H), 8.48 (d, 1H), 8.17 (m, 3H), 7.84 (m, 1H), 7.63 (m, 2H), 7.43 (d, 2H), 7.33 (m, 4H), 5.61 (s, 2H), 4.03 (t, 2H), 1.32 (m, 2H), 0.56 (t, 3H).

Example 9

N-{2-[1-(4-chlorobenzyl)-1H-indol-3-yl]-2-oxoacetyl}-N-quinolin-6-ylpropionamide (7)

$^1$H NMR (600 MHz, DMSO-D6) δ=9.03 (m, 1H), 8.52 (s, 1H), 8.45 (d, 1H), 8.23 (d, 2H), 8.18 (d, 1H), 8.13 (m, 1H), 7.88 (m, 1H), 7.65 (m, 1H), 7.58 (m, 1H), 7.45 (d, 2H), 7.30 (m, 4H), 5.59 (s, 2H), 2.61 (q, 3H), 0.88 (t, 3H).

Example 10

Ethyl {2-[1-(4-chlorobenzyl)-1H-indol-3-yl]-2-oxoacetyl}pyridin-4-ylcarbamate (8)

m.p.: 62° C.

$^1$H NMR (500 MHz, DMSO-D6) δ=8.74 (m, 2H), 8.52 (s, 1H), 8.12 (m, 1H), 7.60 (m, 1H), 7.55 (m, 2H), 7.40 (m, 2H), 7.30 (m, 4H), 5.57 (s, 2H), 4.10 (q, 2H), 0.95 (t, 3H).

Example 11

Comparison Substance

Preparation of 2-[1-(4-chlorobenzyl)-1H-indol-3-yl]-N-(2-methylquinolin-6-yl)-2-oxoacetamide (9)

Yield: 14.8 g (77.3% of theory)

m.p.: 182–185° C.

$^1$H-NMR (CDCl$_3$) δ=9.58 (s, 1H), 9.12 (s, 1H), 8.5 (s, 1H), 8.41 (s, 1H), 8.05 (t, 2H), 7.78 (d, 1H), 7.4 (dd, 1H), 7.32 (m, 4H), 7.26 (s, 1H), 7.15 (d, 1H), 5.38 (s, 2H), 2.73 (s, 3H) ppm Example 12

Comparison Substance

2-[1-(4-Chlorobenzyl)-1H-indol-3-yl]-2-oxo-N-quinolin-6-ylacetamide (10)

m.p.: 200° C.

$^1$H-NMR (DMSO-D$_6$) δ=11.5 (s, 1H), 9.05 (s, 1H), 8.85 (s, 1H), 8.66 (s, 1H), 8.32 (d, 2H), 8.12 (d, 1H), 8.03 (d, 1H), 7.63 (d, 1H), 7.53 (dd, 1H), 7.42 (d, 2H), 7.30–7.38 (m, 4H), 5.63 (s, 2H) ppm

Example 13

Comparison Substance

2-[1-(4-Chlorobenzyl)-1H-indol-3-yl]-2-oxo-N-quinolin-8-ylacetamide (12)

m.p.: 178° C.

Example 14

Comparison Substance

2-[1-(4-Chlorobenzyl)-1H-indol-3-yl]-N-isoquinolin-5-yl-2-oxoacetamide (13)

m.p.: 239–241° C.

Example 15

Comparison Substance

2-[1-(4-Chlorobenzyl)-1H-indol-3-yl]-2-oxo-N-pyridin-4-ylacetamide (14)

m.p.: 264° C.

Example 16

Comparison Substance

2-[1-(4-Fluorobenzyl)-1H-indol-3-yl]-N-(2-methylquinolin-8-yl)-2-oxoacetamide (15)

m.p.: 200–202° C.

Biological effects of the compounds according to the invention

Carrying out in-vitro and in-vivo tests on selected tumor models showed the presence of the following pharmacological activities.

Example 17

Antiproliferative Effect on Various Tumor Cell Lines

The antiproliferative activity of substances 1, 2, 4, 9, 11, 12, 13 and 15 was investigated in a proliferation test performed on established tumor cell lines (D. A. Scuderio et al. Cancer Res. 1988, 48, 4827–4833). The test which is used determines the cellular dehydrogenase activity and makes it possible to determine cell viability and determine cell number indirectly. The cell lines which are used are the human cervical carcinoma cell line KB/HeLa (ATCC CCL17), the ovarian adenocarcinoma cell line SKOV-3 (ATCC HTB77), the human glioblastoma cell line SF-268 (NCI 503138) and the lung carcinoma cell line NCI-H460 (NCI 503473).

TABLE 1

Ability of the substances according to the invention to inhibit proliferation in the XTT cytotoxicity test carried out on human tumor cell lines

| | XTT proliferation assay, EC50 in µg/ml | | | |
|---|---|---|---|---|
| Example | KB/HeLa | SKOV3 | SF-268 | NCI-H460 |
| 1 | 0.045 | 0.029 | 0.042 | 0.046 |
| 2 | 0.202 | 0.123 | 0.166 | 0.168 |
| 4 | 0.335 | 0.144 | >3.16 | 0.233 |
| 11 | 0.036 | 0.029 | 0.036 | 0.057 |
| 9 (C) | 0.183 | 0.174 | 0.261 | 0.344 |
| 12 (C) | >3.16 | >3.16 | >3.16 | >3.16 |
| 13 (C) | >3.16 | >3.16 | >3.16 | >3.16 |
| 15 (C) | >3.16 | n.d. | >3.16 | n.d. |

C = Comparison substance;
n.d.: not determined

The results show that implementation examples 1, 2, 4 and 11 are very potent inhibitors of the proliferation of selected tumor cell lines.

Example 18

Antiproliferative Effect on MDR Tumor Cell Lines

For further characterization, substances 1, 2, 4 and 11 were investigated with regard to their effect on mulitdrug-resistance cell lines as compared with that on nonresistant wild-type cell lines.

The cell lines which were investigated are the murine cell line L1210, the acute myeloid leukemia cell line LT12 and the resistant lines L1210/mdr and LT12/mdr. The murine cell line P388 (methylcholanthrene-induced lymphoid neoplasm) and doxorubicin-resistant P388 were also included as test systems.

The test results are summarized in Table 2 below:

XTT proliferation assay, $EC_{50}$ in µg/ml

TABLE 2

Inhibitory effect of the substances on human tumor cell lines in the XTT proliferation test.

| Example | LT12 | LT12mdr | L1210 | L1210VCR | P388 | P388ADR |
|---|---|---|---|---|---|---|
| 1 | 0.015 | 0.017 | 0.018 | 0.021 | 0.012 | 0.019 |
| 2 | 0.225 | 0.272 | 0.206 | 0.558 | 0.224 | 0.215 |
| 4 | 0.084 | 0.093 | 0.246 | 0.241 | 0.175 | 0.231 |
| 11 | 0.023 | 0.054 | 0.052 | 0.067 | 0.018 | 0.051 |
| Paclitaxel | 0.005 | 0.34 | 0.048 | >3.16 | 0.035 | >3.16 |
| Vincristine | 0.002 | 0.134 | 0.015 | >3.16 | 0.004 | 0.93 |
| Doxorubicin | 0.029 | >3.16 | 0.269 | >3.16 | 0.204 | >3.16 |
| Mitoxantrone | 0.006 | 3.1 | 0.09 | 2.1 | 0.053 | 0.608 |
| Etoposide | 0.094 | >3.6 | 0.269 | >3.16 | 0.202 | >3.16 |

C = Comparison example

Substances 1, 2, 4 and 11 exhibit a very potent inhibitory effect on all the cell lines tested, while the classic substances which have a tubulin-inhibiting effect, such as paclitaxel or vincristine, and the topoisomerase II inhibitors (doxorubicin, mitoxantrone and etoposide) can be seen to have an effect on the MDR1-resistant cell lines which is at least greatly reduced.

Example 19

Inhibition of Tubulin Polymerization

Substances 1, 4, 9, 11, 12, 13 and 15 were tested for their ability to inhibit the polymerization of bovine tubulin in an in-vitro test (D. M. Bollag et al. Cancer Res. 1995, 55, 2325–2333). This test uses-tubulin which has been purified by cycles of polymerization and depolymerization and which is caused to polymerize by adding GTP and heating it. Table 3 gives the $EC_{50}$ values causing inhibition of the polymerization of tubulin containing 30% associated proteins (MPAs).

TABLE 3

Inhibition of tubulin polymerization. Mean values of two independent experiments.

| Example | Inhibition of tubulin polymerization, EC50 in µg/ml |
|---|---|
| 1 | 0.71 |
| 4 | 1.26 |
| 11 | 0.97 |
| 9 (C) | 1.16 |
| 12 (C) | >10 µM |
| 13 (C) | >10 µM |
| 15 (C) | >10 µM |
| Vincristine | 0.35 |

C = Comparison example

The results (see Table 3) show that substances 1, 4, 9 and 11 have a very potent inhibitory effect on tubulin polymerization while compounds 12, 13 and 15 do not exert any effect.

Example 20

Inhibition of Topoisomerase II

The ability of substance 1 to inhibit topoisomerase II was examined in two different in-vitro tests.

kDNA Assay for Testing Topoisomerase II Activity:

In this assay, which was described by P. Arimondo (Anti-Cancer Drug Design 2000, 15(6), 413–421), kDNA is treated with human DNA topoisomerase II in the absence or presence of the test compounds. In the assay, compound 1 according to the invention was tested at three different concentrations (100, 31.6 and 10 µM). A positive control and the reference compounds m-amsacrine (m-amsa), paclitaxel (Taxol) and vincristine, with the concentration in each case being 100 µM, were used for comparison.

Implementation of the Assay:

2 µL of 10× assay buffer, 1 µL of kDNA (200 ng), 0.5 µL of human topoisomerase II (1 unit) and 15.5 µL of $H_2O$ are added by pipette to 1 µL of initially introduced test substance (20 times concentrated in 100% DMSO) and the reagents are mixed.

Figure 2:
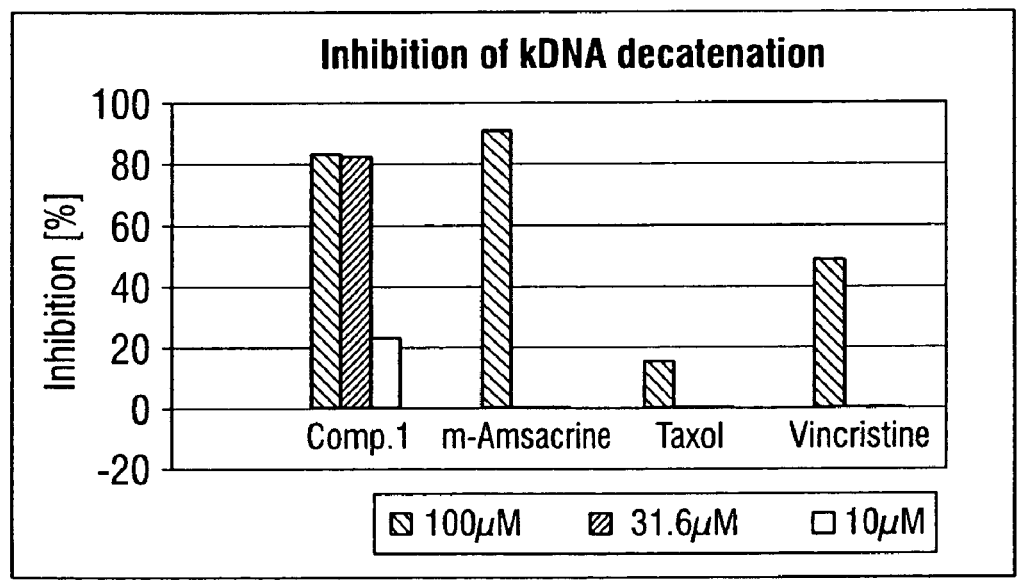
FIG. 2 is a graphic illustration of inhibition of kDNA decatenation.

The reaction assay samples are placed in a heating block which has been preheated to 37° C. and incubated at 37° C. for 10 min. The incubation is stopped after adding 4 µL of 5× Stop buffer and the substance is subsequently extracted with CIA. After that, 20 µL of the supernatant are loaded onto a 1% agarose gel containing 0.25 µg of ethidium bromide/mL and separated at 100 V for 1 h. Finally, the gel is photographed under UV excitation (see FIG. 1). The inhibition of the decatenation of kDNA is quantified using the GelPro® Analyzer Software (see FIG. 2).

pRYG Relaxation Assay for Testing Topoisomerase II Activity:

This relaxation assay was used to further demonstrate the inhibitory properties of the compounds according to the invention on topoisomerase II. In the assay, the compound 1 according to the invention was tested at three different concentrations (100, 31.6 and 10 µM). The reference compounds m-amsacrine, paclitaxel (Taxol) and vincristine were used, at concentrations of 316 and 100 µM, for comparison.

Figure 3:
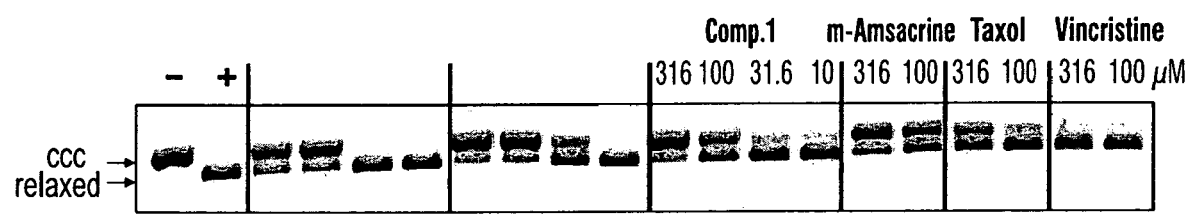
FIG. 3 is a photograph of pRYG relaxation assay.
Figure 4:
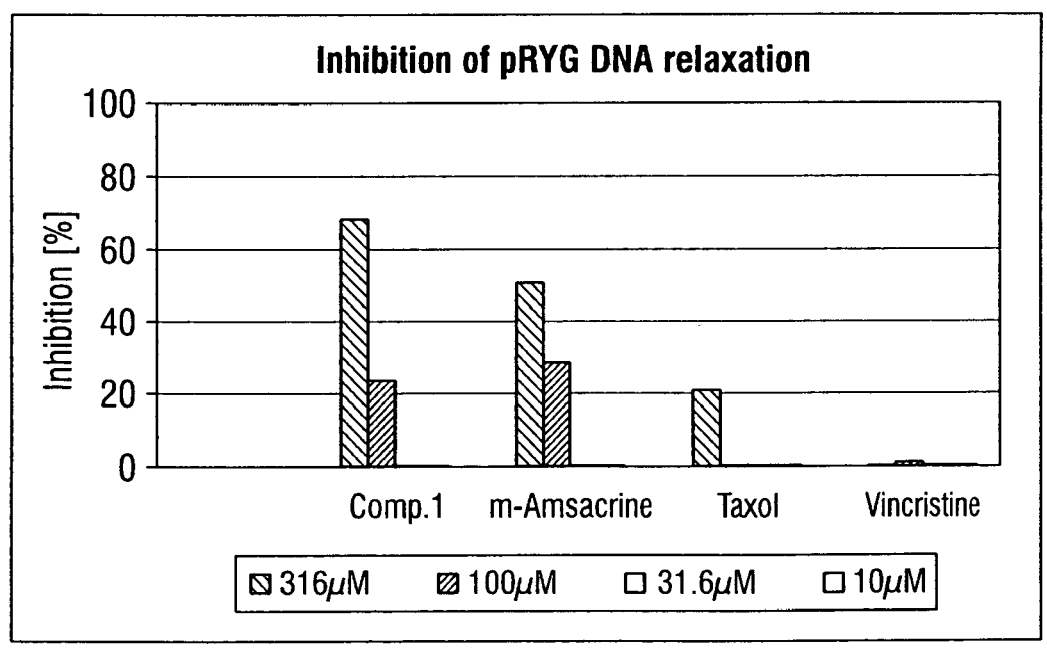
FIG. 4 is a graphic illustration of inhibition of pRYG DNA relaxation.

The assay is carried out as follows:

2 µL of 10× assay buffer, 0.5 µL of pRYG DNA (125 ng), 0.5 µL of human topoisomerase II (1 unit) and 16 µL of $H_2O$ are added by pipette to 1 µL of initially introduced test substance (20 times concentrated in 100% DMSO) and the reagents are mixed. The reaction assay samples are placed in a heating block which has been preheated to 37° C. and incubated at 37° C. for 30 min. The incubation is stopped after adding 4 µL of 5× Stop buffer. After that, 10 µL of the assay sample are loaded onto a 1.2% agarose gel containing 0.25 µg of ethidium bromide/mL and separated at 100 V for 2.5 h. Finally, the gel is photographed under UV excitation (see FIG. 3). The inhibition of pRYG relaxation is quantified using the GelPro® Analyzer Software (see FIG. 4).

Taken overall, it can be stated that compound 1 according to the invention was shown to significantly inhibit topoisomerase II in both assays. The results obtained with compound 1 are comparable with the inhibition values obtained with the topoisomerase II inhibitor m-amsacrine. As expected, neither paclitaxel nor vincristine was observed to have any inhibitory effects in the two assays.

Example 21

Cell Cycle Analysis

The cell cycle comprises the progress of the cell from one cell generation to the next.

During the resting phase (G0) and presynthetic phase (G1), the cell possesses a diploid set of chromosomes (2c). In the synthetic phase (S), the quantity of DNA is increased by replication. The S phase ends when the premitotic phase (G2M), in which the cell possesses a reduplicated complement of chromosomes (4c) and a doubled content of DNA, is reached. In the subsequent mitotic phase (M), which is of short duration, the reduplicated chromosomes are uniformly apportioned between two daughter cells, which then in each case once again possess a diploid content of DNA and are in the G01 phase, which means that the cell cycle can begin afresh.

For the cell cycle analysis, KB/HeLa cells were treated with different concentrations of the test substances (0.1–1000 nM) at 37° C. for 24 hours.

The percentage of cells arrested in the G2/M phase of the cell cycle after having been treated with reference substances or selected test substances is shown in Table 4 below. The results were analyzed using special analytical software (ModFit™).

TABLE 4

Concentration required for inhibiting 50% of the cells in the G2/M phase.

| Example | EC50 in nM (50% of cells in G2/M) |
|---|---|
| 1 | 25.2 |
| 2 | 125.3 |
| 4 | 252 |
| 11 | 41.8 |
| 14 (C) | >1000 |
| paclitaxel | 26.9 |
| mitoxantrone | 25.3 |

Compounds 1, 2, 4 and 11 according to the invention exhibit activities which are comparable to those of the reference compounds paclitaxel and mitoxantrone.

Example 22

Demonstration of Apoptosis $CDD^{plus}$ Nucleosome ELISA Test:

Nuclear fragmentation is a late consequence of apoptotic processes. The changes which can be observed in this connection can be attributed to DNA strands being cleaved by endonucleases and the fragmentation into nucleosome particles which results therefrom.

The $CDD^{plus}$ nucleosome ELISA test described by Roche Molecular Biochemicals was used for demonstrating the nucleosome particles.

Figure 5:
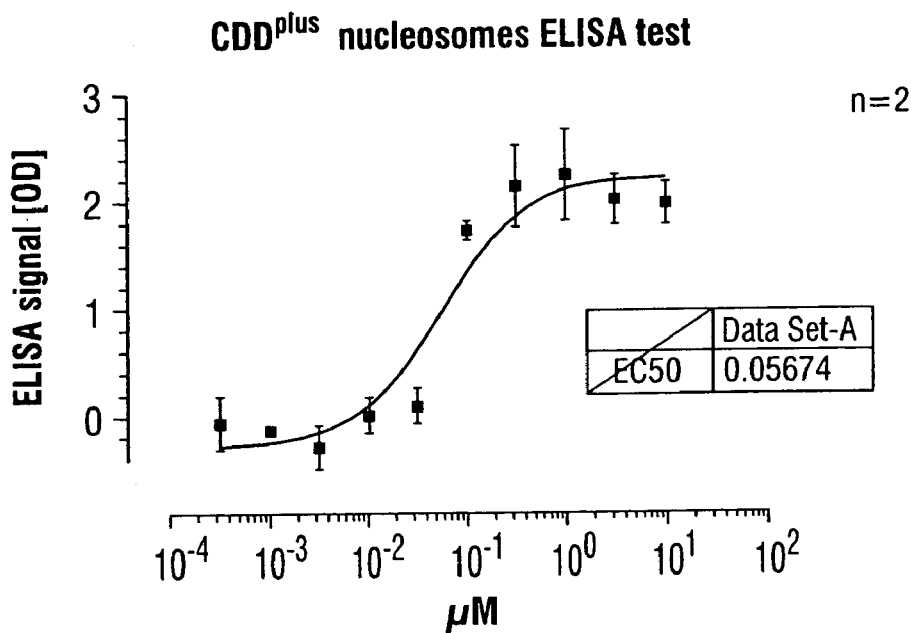
FIG. 5 is a graphic illustration of CDD$^{plus}$ nucleosomes ELISA test for Compound 1.
Figure 6:
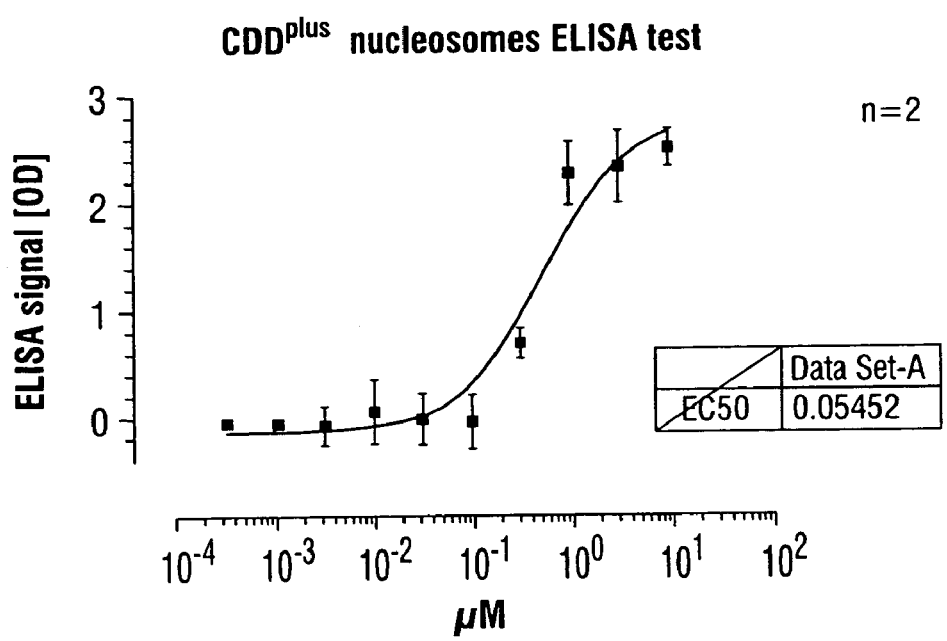
FIG. 6 is a graphic illustration of CDD$^{plus}$ nucleosomes ELISA test for Compound 2.

For this, the effects of compounds 1 and 2 on the U-937 cell line were investigated at different concentrations (1 nM–10 μM; 24 h of treatment). (See FIG. 5 and FIG. 6).

In this test, it was possible to observe a concentration-dependent increase of nucleosomes in the cell lysate for compounds 1 and 2. It was not possible to demonstrate any significant increase in the cell culture supernatant, which is evidence in support of, apoptotic cell death occurring after treatment with 1 and 2.

Example 23

Demonstration of the Saturation Solubility in Water of the Compounds According to the Invention The saturation solubility in water of compounds 1, 2, 10 and 14 was determined as described below. A maximum of 1% DMSO was added for the purpose of solubilizing the substances and improving the wetting of the samples. An HPLC-UV method was used for checking the content. The results are summarized in Table 5 below:

TABLE 5

Saturation solubilities of compounds 1, 2, 10 and 14

| Name of compound | Saturation solubility in water [μg/ml] |
|---|---|
| 1 | 25.0 |
| 2 | 28.5 |
| 10 (C) | 0.038 |
| 14 (C) | 0.35 |

Compounds 1 and 2 according to the invention differ from compounds 10 and 14 in being more soluble in water.

Example 24

In-vivo Activity

The in-vivo activity and tolerability of compound 2 according to the invention, as compared with those of substances 10 and 14, were examined in a human xenograft model (melanoma, MEXF-462). The results are summarized in Table 6 below:

In-vivo activities of compounds 2, 10 and 14 (melanoma; MEXF462)

TABLE 6

In-vivo activities of compounds 2, 10 and 14 (melanoma; MEXF462)

| Compound | Dose [mg/kg] | Administration | Deaths n[1] | Optimum T/C % (day) |
|---|---|---|---|---|
| 2 | 80 | p.o. | 0/6 mice | 0.0% (18) complete remission in the case of all 6 animals |
| 10 (C) | 70 | p.o. | 5/6 mice dead | 2.3% (7) |
| 10 (C) | 55 | p.o. | 2/6 mice dead | 0.8% (14) |
| 14 (C) | 32 | p.o. | 3/5 mice dead | 14.6% (7) |
| 14 (C) | 16 | p.o. | 3/5 mice dead | 0.7% (18) |

[1]Number of dead animals as compared with the total number

In this xenograft model, compound 2 was observed to produce complete remission of the tumors in the treated animals while also being very well tolerated (no deaths). While comparable antineoplastic effects were observed in the case of compounds 10 and 14, these latter compounds were less well tolerated.

Example 25

In-vivo Activity

The in-vivo activity and tolerability of compound 2 according to the invention, as compared with those of substance 10, were examined in another human xenograft model (mammary gland, MAXF857).

The results are shown in the following table:

Effect of 2 and 10 on the mammary cancer MAXF857

TABLE 7

In-vivo activities of compounds 2 and 10 (mammary gland; MAXF857)

| Compound | Dose [mg/kg] | Administration | Deaths n[1] | Optimum T/C % (day) |
|---|---|---|---|---|
| 2 | 80 | p.o. | 0/6 mice | 9.6% (10) |
| 10 (C) | 40 | p.o. | 2/6 mice dead | 6.5% (10) |

[1]Number of dead animals as compared with the total number

While compounds 2 and 10 were observed to have comparable antineoplastic effects, substance 10 (2/6 mice dead) is substantially less well tolerated than 2.

We claim:
1. An indole derivative of the general formula (I)

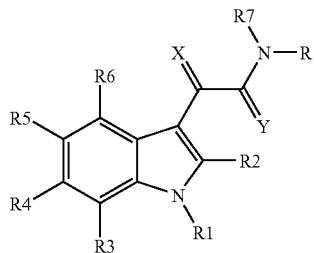

formula I wherein
R: is a saturated, unsaturated or aromatic, substituted or unsubstituted ($C_2$–$C_{14}$)-heterocycle which contains one or more heteroatoms selected from the group N, O and S and is linked directly to the amide nitrogen,
R1: is unsubstituted or substituted alkyl-aryl,
R2: is
  (i) hydrogen,
  (ii) unsubstituted or substituted ($C_1$–$C_6$)-alkyl,
R3–R6: are
  (i) hydrogen
  (ii) unsubstituted or substituted ($C_1$–$C_6$)-alkyl,
  (iii) unsubstituted or substituted ($C_3$–$C_7$)-cycloalkyl,
  (iv) amino, mono-($C_1$–$C_4$)-alkylamino, di-($C_1$–$C_4$)-alkylamino,
  (v) halogen,
  (vi) ($C_1$–$C_4$)-alkyl which is substituted by one or more fluorine atoms,
  (vii) cyano, straight-chain or branched cyano-($C_1$–$C_6$)-alkyl,
  (viii) ($C_1$–$C_6$)-alkylcarbonyl,
  (ix) carboxyl, ($C_1$–$C_4$)-alkoxycarbonyl, carboxy-($C_1$–$C_6$)-alkyl or ($C_1$–$C_6$)-alkoxycarbonyl-($C_1$–$C_6$)-alkyl,
  (x) hydroxyl,
  (xi) —($C_1$–$C_6$)-alkoxy,
  (xii) aryl-($C_1$–$C_4$)-alkoxy, preferably benzyloxy,
  (xiii) ($C_1$–$C_6$)-alkoxycarbonylamino, ($C_1$–$C_6$)-alkoxycarbonylamino-($C_1$–$C_6$)-alkyl,
R7: is
  ($C_1$–$C_6$)-alkylcarbonyl or ($C_1$–$C_6$)-alkoxy-carbonyl
and
X, Y: are oxygen or sulfur,
  with the proviso that, when R is an unsubstituted or substituted 2-, 3-, 4-, 5- or 6-pyridyl group and R1–R6 have the abovementioned meaning, R7 is not an acetyl radical or a tert-butyloxycarbonyl group; the tautomers, stereoisomers, including the diastereomers and enantiomers, thereof, and also the physiologically tolerated salts thereof.

2. An indole derivative as claimed in claim 1, wherein R is
  (i) unsubstituted or substituted 5-, 6-, 7-quinolyl,
  (ii) unsubstituted or substituted 2-, 3-, 6-, 7- and 8-pyridopyrazinyl,
  (iii) unsubstituted or substituted 3-, 4-, 5-, 6- and 7-indazolyl,
  (iv) unsubstituted or substituted 2-, 3-, 4-, 5- and 6-pyridyl,
  (v) unsubstituted or substituted 3-, 4- and 5-isoxazolyl,
  (vi) unsubstituted or substituted 3-, 4- and 5-isothiazolyl.

3. An indole derivative as claimed in claim 1, wherein R7 is methoxycarbonyl, ethoxycarbonyl, propoxycarbonyl, acetyl or propionyl.

4. An indole derivative as claimed in claim 1, wherein the compounds of the general formula I is selected from the following group of compounds:
  N-{2-[1-(4-chlorobenzyl)-1H-indol-3-yl]-2-oxoacetyl}-N-quinolin-6-ylacetamide (2),
  methyl {2-[1-(4-chlorobenzyl)-1H-indol-3-yl]-2-oxoacetyl}quinolin-6-ylcarbamate (3),
  ethyl {2-[1-(4-chlorobenzyl)-1H-indol-3-yl]-2-oxoacetyl}quinolin-6-ylcarbamate (5),
  propyl {2-[1-(4-chlorobenzyl)-1H-indol-3-yl]-2-oxoacetyl}quinolin-6-ylcarbamate (6),
  N-{2-[1-(4-chlorobenzyl)-1H-indol-3-yl]-2-oxoacetyl}-N-quinolin-6-ylpropionamide (7), and
  ethyl {2-[l-(4-chlorobenzyl)-1H-indol-3-yl]-2-oxoacetyl}pyridin-4-ylcarbamate (8).

5. An indole derivative as claimed in claim 1, wherein R1 is 4-chlorobenzyl, R2–R6 are hydrogen and X, Y are oxygen or sulfur.

6. An indole derivative as claimed in claim 1, wherein R3, R4, R5 or R6 is trifluoromethyl.

7. An indole derivative of the general formula Ia,

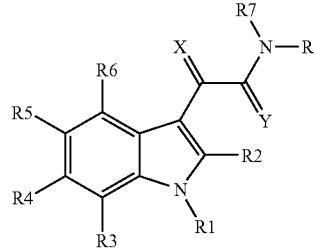

formula Ia wherein
R: is, directly linked to the amide nitrogen,
  (i) substituted 6-quinolyl, unsubstituted or substituted 7-quinolyl, where 2-methyl-6-quinolyl is excluded and where, when X is a sulfur atom, R can also be unsubstituted 6-quinolyl,
  (ii) unsubstituted or substituted 2-, 3-, 6-, 7- and 8-pyridopyrazinyl,
  (iii) unsubstituted or substituted 3-, 4-, 5-, 6- and 7-indazolyl,
R1: is unsubstituted or substituted alkyl-aryl, R2: is hydrogen,
R3–R6: are
  (i) hydrogen
  (ii) unsubstituted or substituted ($C_1$–$C_6$)-alkyl,
  (iii) unsubstituted or substituted ($C_3$–$C_7$)-cycloalkyl,
  (iv) amino, mono-($C_1$–$C_4$)-alkylamino, di-($C_1$–$C_4$)-alkylamino,
  (v) halogen, (vi) ($C_1$–$C_4$)-alkyl which is substituted by one or more fluorine atoms, preferably trifluoromethyl group,
  (vii) cyano, straight-chain or branched cyano-($C_1$–$C_6$)-alkyl,
  (viii) ($C_1$–$C_6$)-alkylcarbonyl,
  (ix) carboxyl, ($C_1$–$C_4$)-alkoxycarbonyl, carboxy-($C_1$–$C_6$)-alkyl or ($C_1$–$C_6$)-alkoxycarbonyl-($C_1$–$C_6$)-alkyl, (x) —(C$_1$–C$_6$)-alkoxy, (xi) aryl-(C$_1$–C$_4$)-alkoxy, preferably benzyloxy, (xii) (C$_1$–C$_6$)-alkoxycarbonylamino, (C$_1$–C$_6$)-alkoxycarbonylamino-(C$_1$–C$_6$)-alkyl, and R7: hydrogen and X, Y: are oxygen or sulfur, the tautomers and stereoisomers, including the diastereomers and enantiomers, thereof, and also the physiologically tolerated salts thereof.

8. An indole derivative as claimed in claim 7, wherein the compound of the general formula I is selected from the following group of compounds:

2-[1-(4-chlorobenzyl)-1H-indol-3-yl]-N-quinolin-6-yl-2-thioxoacetamide (11),

2-[1-(4-chlorobenzyl)-1H-indol-3-yl]-2-oxo-N-pyrido[2,3-b]pyrazin-7-ylacetamide (1), and 2-[1-(4-chlorobenzyl)-1H-indol-3-yl]-N-(1H-indazol-5-yl)-2-oxoacetamide (4).

9. An indole derivative as claimed in claim 7, wherein R1 is 4-chlorobenzyl, R2–R6 are hydrogen and X, Y are oxygen or sulfur.

10. A pharmaceutical composition which comprises at least one of the indole derivatives as claimed in claim 1.

11. A pharmaceutical composition as claimed in claim 10 which comprises the indole derivative in a microparticulate or nanoparticulate composition.

12. A pharmaceutical composition as claimed in claim 10 which comprises the indole derivative and a pharmaceutically utilizable carrier and/or diluent and auxiliary substance in the form of tablets, sugar-coated tablets, capsules, solutions for infusion or ampoules, suppositories, plasters, powder preparations which can be used inhalatively, suspensions, creams and ointments.

13. A method for treating a tumor disease selected from the group consisting of sarcoma, adenocarcinoma, melanoma, lymphoma, leukemia, non Hodgkin's lymphonia, Hodgkin's disease, breast cancer, ovarian cancer, transitional cell bladder carcinoma, small cell lung cancer, multiple myeloma, kaposi's sarcoma, cervical cancer, pancreatic cancer, testicular carcinoma, acute lymphatic leukemia (ALL), rhabdomyo sarcoma, euroblastoms, Wilm's tumor, medulloblastoma, choriocarcinoma, and non-small cell lung cancer, cervical carcinoma, ovarial adenocarcinoma, glioblastoma, lung carcinoma, breast cancer, melanoma, colon cancer and blood cancer, which comprises administering an indole derivative as claimed in claim 1 to an individual in need of the treatment.

14. The method as claimed in claim 13, wherein the tumor disease involves drug resistance against at least one other active compound.

15. The method as claimed in claim 13, wherein the tumor disease involves a metastasizing carcinoma.

16. A pharmaceutical composition which comprises at least one of the indole derivatives of the general formula Ia:

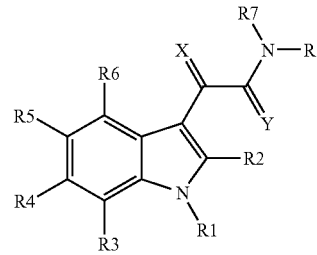

formula Ia wherein

R: is, directly linked to the amide nitrogen, (i) substituted 6-quinolyl, unsubstituted or substituted 7-quinolyl, where 2-methyl-6-quinolyl is excluded and where, when X is a sulfur atom, R can also be unsubstituted 6-quinolyl, (ii) unsubstituted or substituted 2-, 3-, 6-, 7- and 8-pyridopyrazinyl, (iii) unsubstituted or substituted 3-, 4-, 5-, 6- and 7-indazolyl, R1: is unsubstituted or substituted alkyl-aryl, R2: is hydrogen, R3–R6: are (i) hydrogen (ii) unsubstituted or substituted (C$_1$–C$_6$)-alkyl, (iii) unsubstituted or substituted (C$_3$–C$_7$)-cycloalkyl, (iv) amino, mono-(C$_1$–C$_4$)-alkylamino, di-(C$_1$–C$_4$)-alkylamino, (v) halogen, (vi) (C$_1$–C$_4$)-alkyl which is substituted by one or more fluorine atoms, preferably trifluoromethyl group, (vii) cyano, straight-chain or branched cyano-(C$_1$–C$_6$)-alkyl, (viii) (C$_1$–C$_6$)-alkylcarbonyl, (ix) carboxyl, (C$_1$–C$_4$)-alkoxycarbonyl, carboxy-(C$_1$–C$_6$)-alkyl or (C$_1$–C$_6$)-alkoxycarbonyl-(C$_1$–C$_6$)-alkyl, (x) —(C$_1$–C$_6$)-alkoxy, (xi) aryl-(C$_1$–C$_4$)-alkoxy, preferably benzyloxy, (xii) (C$_1$–C$_6$)-alkoxycarbonylamino, (C$_1$–C$_6$)-alkoxycarbonylamino-(C$_1$–C$_6$)-alkyl, and R7: hydrogen and X, Y: are oxygen or sulfur, the tautomers and stereoisomers, including the diastereomers and enantiomers, thereof, and also the physiologically tolerated salts thereof.

17. A pharmaceutical composition as claimed in claim 16 which comprises the indole derivative in a microparticulate or nanoparticulate composition.

18. A pharmaceutical composition as claimed in claim 16 which comprises the indole derivative and a pharmaceutically utilizable carrier and/or diluent and auxiliary substance in the form of tablets, sugar-coated tablets, capsules, solutions for infusion or ampoules, suppositories, plasters, powder preparations which can be used inhalatively, suspensions, creams and ointments.

19. A method for treating a tumor disease selected from the group consisting of sarcoma, adenocarcinoma, melanoma, lymphoma, leukemia, non Hodgkin's lymphonia, Hodgkin's disease, breast cancer, ovarian cancer, transitional cell bladder carcinoma, small cell lung cancer, multiple myeloma, kaposi's sarcoma, cervical cancer, pancreatic cancer, testicular carcinoma, acute lymphatic leukemia (ALL), rhabdomyo sarcoma, euroblastoms, Wilm's tumor, medulloblastoma, choriocarcinoma, and non-small cell lung cancer, cervical carcinoma, ovarial adenocarcinoma, glioblastoma, lung carcinoma, breast cancer, melanoma, colon cancer and blood cancer, which comprises administering an indole derivative of the general formula Ib:

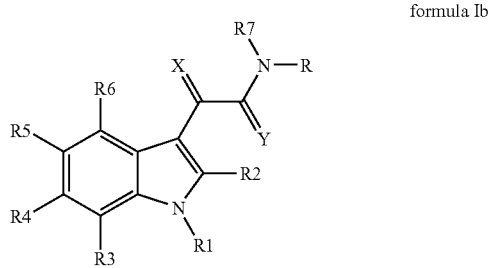

formula Ib wherein
- R: is, directly linked to the amide nitrogen,
  - (i) unsubstituted or substituted 2-, 3-, 6-, 7- and 8-pyridopyrazinyl,
  - (ii) unsubstituted or substituted 3-, 4-, 5-, 6- and 7-indazolyl,
- R1: is unsubstituted or substituted alkyl-aryl, R2: is hydrogen,
- R3–R6: are
  - (i) hydrogen
  - (ii) unsubstituted or substituted $(C_1-C_6)$-alkyl,
  - (iii) unsubstituted or substituted $(C_3-C_7)$-cycloalkyl,
  - (iv) amino, mono-$(C_1-C_4)$-alkylamino, di-$(C_1-C_4)$-alkylamino,
  - (v) halogen, (vi) $(C_1-C_4)$-alkyl which is substituted by one or more fluorine atoms, preferably trifluoromethyl group,
  - (vii) cyano, straight-chain or branched cyano-$(C_1-C_6)$-alkyl,
  - (viii) $(C_1-C_6)$-alkylcarbonyl,
  - (ix) carboxyl, $(C_1-C_4)$-alkoxycarbonyl, carboxy-$(C_1-C_6)$-alkyl or $(C_1-C_6)$-alkoxycarbonyl-$(C_1-C_6)$-alkyl,
  - (x) —$(C_1-C_6)$-alkoxy,
  - (xi) aryl-$(C_1-C_4)$-alkoxy, preferably benzyloxy,
  - (xii) $(C_1-C_6)$-alkoxycarbonylamino, $(C_1-C_6)$-alkoxycarbonylamino-$(C_1-C_6)$-alkyl,
- and
- R7: hydrogen
- and
- X, Y: are oxygen or sulfur,
  - the tautomers and stereoisomers, including the diastereomers and enantiomers, thereof, and also the physiologically tolerated salts thereof.

20. The method as claimed in claim 19, wherein the tumor disease involves drug resistance against at least one other active compound.

21. The method as claimed in claim 19, wherein the tumor disease involves a metastasizing carcinoma.

* * * * *

UNITED STATES PATENT AND TRADEMARK OFFICE
CERTIFICATE OF CORRECTION

PATENT NO. : 7,205,299 B2 Page 1 of 1
APPLICATION NO. : 10/858751
DATED : April 17, 2007
INVENTOR(S) : Gerlach et al.

It is certified that error appears in the above-identified patent and that said Letters Patent is hereby corrected as shown below:

On title page Item [75]
Please correct the spelling of inventor: Peter Emig to Peter Ernig Signed and Sealed this Twenty-second Day of May, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,205,299 B2 | Page 1 of 1 |
| APPLICATION NO. | : 10/858751 | |
| DATED | : April 17, 2007 | |
| INVENTOR(S) | : Gerlach et al. | |

It is certified that error appears in the above-identified patent and that said Letters Patent is hereby corrected as shown below:

On title page Item [75]
Please correct the spelling of inventor: Peter Ernig to Peter Emig This certificate supersedes Certificate of Correction issued May 22, 2007.

Signed and Sealed this

Twenty-fourth Day of July, 2007

JON W. DUDAS
*Director of the United States Patent and Trademark Office*